US006545028B2

(12) United States Patent
Jensen et al.

(10) Patent No.: US 6,545,028 B2
(45) Date of Patent: *Apr. 8, 2003

(54) CHEMICAL COMPOUNDS HAVING ION CHANNEL BLOCKING ACTIVITY FOR THE TREATMENT OF IMMUNE DYSFUNCTION

(75) Inventors: Bo S. Jensen, København S (DK); Søren-Peter Olsen, Klampenborg (DK); Tino D. Jørgensen, Solrød Strand (DK); Dorte Strøbæk, Farum (DK); Palle Christophersen, Ballerup (DK); Niels Ødum, København (DK)

(73) Assignee: NeuroSearch A/S, Ballerup (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,645
(22) Filed: Apr. 14, 2000
(65) Prior Publication Data US 2002/0119989 A1 Aug. 29, 2002

Related U.S. Application Data

(63) Continuation of application No. PCT/DK98/00490, filed on Nov. 13, 1998.

(30) Foreign Application Priority Data

Nov. 14, 1997 (DK) .............................. 1298/97
Mar. 19, 1998 (DK) .............................. 0386/98

(51) Int. Cl.⁷ ................ A61K 31/44; A61K 31/50; A61K 31/495; A61K 31/41; A61K 31/415
(52) U.S. Cl. ............... 514/356; 514/252; 514/254.07; 514/383; 514/396; 514/399
(58) Field of Search .................. 514/396, 252, 514/399, 383, 254.07, 356

(56) References Cited

U.S. PATENT DOCUMENTS

| | | | |
|---|---|---|---|
| 3,660,577 A | * | 5/1972 | Buchel et al. |
| 3,799,934 A | | 3/1974 | Meyer et al. |
| 4,073,922 A | * | 2/1978 | Wyburn-Mason |
| 4,267,169 A | * | 5/1981 | Kamishita et al. |
| 4,435,409 A | | 3/1984 | Leibowitz et al. |
| 4,952,594 A | * | 8/1990 | Mercer |
| 5,273,992 A | | 12/1993 | Brugnara et al. |
| 5,478,848 A | * | 12/1995 | Aune |
| 5,670,113 A | | 9/1997 | Akong et al. |

FOREIGN PATENT DOCUMENTS

| | | |
|---|---|---|
| EP | A1531598 | 3/1993 |
| JP | A8225450 | 9/1996 |
| WO | A1-9521943 | 8/1995 |
| WO | A2-9608242 | 3/1996 |
| WO | A1-9735991 | 2/1997 |
| WO | A1-9734589 | 9/1997 |

OTHER PUBLICATIONS

Hamill, O.P., Pflügers Arch., vol. 391 (1981) pp. 85–100.

Akula et al., Drug Design and Delivery, vol. 5, pp. 117–123 (1989).

Wynn et al., Drug Design and Delivery, vol. 3, pp. 245–256 (1988).

Dagnino et al. American Chemical Society, pp. 2524–2529 (1986).

Ramesh et al. Drug Design and Delivery, vol. 2, pp. 79–89 (1987).

Akula et al. Pharmaceutical Research, vol. 7, No. 9, pp. 919–922 (1990).

Ellory et al., Br. J. Pharmacol, pp. 903–905 (1994).

Brugnara et al., The Journal of Pharmacology and Experimental Therapeutics, vol. 273, No. 1, pp. 266–272 (1995).

Brugnara et al., The American Society for Clinical Investigation, Inc. vol. 97, No. 5, pp. 1227–1234 (1996).

Odum et al., The Journal of Immunology, vol. 150, No. 12, pp. 5289–5298 (1993).

Urbahns, Bayer AG, pp. 1 (1998).

Akula et al. Drug Design and Delivery, vol. 7, pp. 11–17 (1990).

Schwab, Ion Channel Modulators, vol. 3, No. 4, pp. 126–129 (1998).

Case et al., Cell Calcium, pp. 1–17 (1997).

Rader et al., T. Cell Activation is Regulated by Voltage–Dependent and Calcium–Activated Potassium Channels, pp. 1425–1430 (1996).

Tacke et al., Immunobiology, pp. 138–139 (1994).

Randriamampita et al., Cell Calcium, pp. 313–323 (1991).

\* cited by examiner

Primary Examiner—William R. A. Jarvis
(74) Attorney, Agent, or Firm—Birch, Stewart, Kolasch & Birch, LLP

(57) ABSTRACT

This invention relates to treatment or alleviation of a disease, condition or disorder selected from inflammatory bowel disease, Chron's disease, colitis ulcerosa, Coeliac disease, dermatitis herpetiformis, dermatomyositis, enteritis allergia, erytherma nodosum leprosum, ileitis regionalis, psoriasis, purpura, scleritis or scleroderma by administering to a living body certain imidazole, triazole, or 1,4-dihydropyridine derivatives.

6 Claims, No Drawings

SEQUENCE LISTING

```
<160> NUMBER OF SEQ ID NOS: 3

<210> SEQ ID NO 1
<211> LENGTH: 1284
<212> TYPE: DNA
<213> ORGANISM: Homo sapiens
<220> FEATURE:
<221> NAME/KEY: CDS
<222> LOCATION: (1)..(1284)

<400> SEQUENCE: 1 atg ggc ggg gat ctg gtg ctt ggc ctg ggg gcc ttg aga cgc cga aag      48
Met Gly Gly Asp Leu Val Leu Gly Leu Gly Ala Leu Arg Arg Arg Lys
  1               5                  10                  15 cgc ttg ctg gag cag gag aag tct ctg gcc ggc tgg gca ctg gtg ctg      96
Arg Leu Leu Glu Gln Glu Lys Ser Leu Ala Gly Trp Ala Leu Val Leu
                 20                  25                  30 gca gga act ggc att gga ctc atg gtg ctg cat gca gag atg ctg tgg     144
Ala Gly Thr Gly Ile Gly Leu Met Val Leu His Ala Glu Met Leu Trp
             35                  40                  45 ttc ggg ggg tgc tcg tgg gcg ctc tac ctg ttc ctg gtt aaa tgc acg     192
Phe Gly Gly Cys Ser Trp Ala Leu Tyr Leu Phe Leu Val Lys Cys Thr
         50                  55                  60 atc agc att tcc acc ttc tta ctc ctc tgc ctc atc gtg gcc ttt cat     240
Ile Ser Ile Ser Thr Phe Leu Leu Leu Cys Leu Ile Val Ala Phe His
 65                  70                  75                  80 gcc aaa gag gtc cag ctg ttc atg acc gac aac ggg ctg cgg gac tgg     288
Ala Lys Glu Val Gln Leu Phe Met Thr Asp Asn Gly Leu Arg Asp Trp
                 85                  90                  95 cgc gtg gcg ctg acc ggg cgg cag gcg gcg cag atc gtg ctg gag ctg     336
Arg Val Ala Leu Thr Gly Arg Gln Ala Ala Gln Ile Val Leu Glu Leu
                100                 105                 110 gtg gtg tgt ggg ctg cac ccg gcg ccc gtg cgg ggc ccg ccg tgc gtg     384
Val Val Cys Gly Leu His Pro Ala Pro Val Arg Gly Pro Pro Cys Val
            115                 120                 125
```

```
cag gat tta ggg gcg ccg ctg acc tcc ccg cag ccc tgg ccg gga ttc          432
Gln Asp Leu Gly Ala Pro Leu Thr Ser Pro Gln Pro Trp Pro Gly Phe
        130                 135                 140 ctg ggc caa ggg gaa gcg ctg ctg tcc ctg gcc atg ctg ctg cgt ctc          480
Leu Gly Gln Gly Glu Ala Leu Leu Ser Leu Ala Met Leu Leu Arg Leu
145                 150                 155                 160 tac ctg gtg ccc cgc gcc gtg ctc ctg cgc agc ggc gtc ctg ctc aac          528
Tyr Leu Val Pro Arg Ala Val Leu Leu Arg Ser Gly Val Leu Leu Asn
                165                 170                 175 gct tcc tac cgc agc atc ggc gct ctc aat caa gtc cgc ttc cgc cac          576
Ala Ser Tyr Arg Ser Ile Gly Ala Leu Asn Gln Val Arg Phe Arg His
            180                 185                 190 tgg ttc gtg gcc aag ctt tac atg aac acg cac cct ggc cgc ctg ctg          624
Trp Phe Val Ala Lys Leu Tyr Met Asn Thr His Pro Gly Arg Leu Leu
        195                 200                 205 ctc ggc ctc acg ctt ggc ctc tgg ctg acc acc gcc tgg gtg ctg tcc          672
Leu Gly Leu Thr Leu Gly Leu Trp Leu Thr Thr Ala Trp Val Leu Ser
210                 215                 220 gtg gcc gag agg cag gct gtt aat gcc act ggg cac ctt tca gac aca          720
Val Ala Glu Arg Gln Ala Val Asn Ala Thr Gly His Leu Ser Asp Thr
225                 230                 235                 240 ctt tgg ctg att ccc atc aca ttc ctg acc atc ggc tat ggt gac gtg          768
Leu Trp Leu Ile Pro Ile Thr Phe Leu Thr Ile Gly Tyr Gly Asp Val
                245                 250                 255 gtg ccg ggc acc atg tgg ggc aag atc gtc tgc ctg tgc act gga gtc          816
Val Pro Gly Thr Met Trp Gly Lys Ile Val Cys Leu Cys Thr Gly Val
            260                 265                 270 atg ggt gtc tgc tgc aca gcc ctg ctg gtg gcc gtg gtg gcc cgg aag          864
Met Gly Val Cys Cys Thr Ala Leu Leu Val Ala Val Val Ala Arg Lys
        275                 280                 285 ctg gag ttt aac aag gca gag aag cac gtg cac aac ttc atg atg gat          912
Leu Glu Phe Asn Lys Ala Glu Lys His Val His Asn Phe Met Met Asp
    290                 295                 300 atc cag tat acc aaa gag atg aag gag tcc gct gcc cga gtg cta caa          960
Ile Gln Tyr Thr Lys Glu Met Lys Glu Ser Ala Ala Arg Val Leu Gln
305                 310                 315                 320 gaa gcc tgg atg ttc tac aaa cat act cgc agg aag gag tct cat gct         1008
Glu Ala Trp Met Phe Tyr Lys His Thr Arg Arg Lys Glu Ser His Ala
                325                 330                 335 gcc cgc agg cat cag cgc aag ctg ctg gcc gcc atc aac gcg ttc cgc         1056
Ala Arg Arg His Gln Arg Lys Leu Leu Ala Ala Ile Asn Ala Phe Arg
            340                 345                 350 cag gtg cgg ctg aaa cac cgg aag ctc cgg gaa caa gtg aac tcc atg         1104
Gln Val Arg Leu Lys His Arg Lys Leu Arg Glu Gln Val Asn Ser Met
        355                 360                 365 gtg gac atc tcc aag atg cac atg atc ctg tat gac ctg cag cag aat         1152
Val Asp Ile Ser Lys Met His Met Ile Leu Tyr Asp Leu Gln Gln Asn
    370                 375                 380 ctg agc agc tca cac cgg gcc ctg gag aaa cag att gac acg ctg gcg         1200
Leu Ser Ser Ser His Arg Ala Leu Glu Lys Gln Ile Asp Thr Leu Ala
385                 390                 395                 400 ggg aag ctg gat gcc ctg act gag ctg ctt agc act gcc ctg ggg ccg         1248
Gly Lys Leu Asp Ala Leu Thr Glu Leu Leu Ser Thr Ala Leu Gly Pro
                405                 410                 415 agg cag ctt cca gaa ccc agc cag cag tcc aag tag                         1284
Arg Gln Leu Pro Glu Pro Ser Gln Gln Ser Lys
            420                 425

<210> SEQ ID NO 2
<211> LENGTH: 427
```

```
<212> TYPE: PRT
<213> ORGANISM: Homo sapiens

<400> SEQUENCE: 2

Met Gly Gly Asp Leu Val Leu Gly Leu Gly Ala Leu Arg Arg Arg Lys
 1               5                  10                  15

Arg Leu Leu Glu Gln Glu Lys Ser Leu Ala Gly Trp Ala Leu Val Leu
                 20                  25                  30

Ala Gly Thr Gly Ile Gly Leu Met Val Leu His Ala Glu Met Leu Trp
             35                  40                  45

Phe Gly Gly Cys Ser Trp Ala Leu Tyr Leu Phe Leu Val Lys Cys Thr
         50                  55                  60

Ile Ser Ile Ser Thr Phe Leu Leu Leu Cys Leu Ile Val Ala Phe His
 65                  70                  75                  80

Ala Lys Glu Val Gln Leu Phe Met Thr Asp Asn Gly Leu Arg Asp Trp
                 85                  90                  95

Arg Val Ala Leu Thr Gly Arg Gln Ala Gln Ile Val Leu Glu Leu
            100                 105                 110

Val Val Cys Gly Leu His Pro Ala Pro Val Arg Gly Pro Pro Cys Val
            115                 120                 125

Gln Asp Leu Gly Ala Pro Leu Thr Ser Pro Gln Pro Trp Pro Gly Phe
        130                 135                 140

Leu Gly Gln Gly Glu Ala Leu Leu Ser Leu Ala Met Leu Leu Arg Leu
145                 150                 155                 160

Tyr Leu Val Pro Arg Ala Val Leu Leu Arg Ser Gly Val Leu Leu Asn
                165                 170                 175

Ala Ser Tyr Arg Ser Ile Gly Ala Leu Asn Gln Val Arg Phe Arg His
            180                 185                 190

Trp Phe Val Ala Lys Leu Tyr Met Asn Thr His Pro Gly Arg Leu Leu
        195                 200                 205

Leu Gly Leu Thr Leu Gly Leu Trp Leu Thr Thr Ala Trp Val Leu Ser
        210                 215                 220

Val Ala Glu Arg Gln Ala Val Asn Ala Thr Gly His Leu Ser Asp Thr
225                 230                 235                 240

Leu Trp Leu Ile Pro Ile Thr Phe Leu Thr Ile Gly Tyr Gly Asp Val
                245                 250                 255

Val Pro Gly Thr Met Trp Gly Lys Ile Val Cys Leu Cys Thr Gly Val
            260                 265                 270

Met Gly Val Cys Cys Thr Ala Leu Leu Val Ala Val Ala Arg Lys
            275                 280                 285

Leu Glu Phe Asn Lys Ala Glu Lys His Val His Asn Phe Met Met Asp
        290                 295                 300

Ile Gln Tyr Thr Lys Glu Met Lys Glu Ser Ala Ala Arg Val Leu Gln
305                 310                 315                 320

Glu Ala Trp Met Phe Tyr Lys His Thr Arg Arg Lys Glu Ser His Ala
                325                 330                 335

Ala Arg Arg His Gln Arg Lys Leu Leu Ala Ala Ile Asn Ala Phe Arg
            340                 345                 350

Gln Val Arg Leu Lys His Arg Lys Leu Arg Glu Gln Val Asn Ser Met
        355                 360                 365

Val Asp Ile Ser Lys Met His Met Ile Leu Tyr Asp Leu Gln Gln Asn
        370                 375                 380

Leu Ser Ser Ser His Arg Ala Leu Glu Lys Gln Ile Asp Thr Leu Ala
385                 390                 395                 400
```

```
Gly Lys Leu Asp Ala Leu Thr Glu Leu Leu Ser Thr Ala Leu Gly Pro
            405                 410                 415

Arg Gln Leu Pro Glu Pro Ser Gln Gln Ser Lys
        420                 425

<210> SEQ ID NO 3
<211> LENGTH: 51
<212> TYPE: PRT
<213> ORGANISM: Artificial Sequence
<220> FEATURE:
<223> OTHER INFORMATION: Query sequence used to identify a cDNA encoding
      the human placenta Ca2+- activated, intermediate conductance
      potassium channel protein via a BLAST search of the EST database

<400> SEQUENCE: 3

Leu Gly His Arg Arg Ala Leu Phe Glu Lys Arg Lys Arg Leu Ser Asp
 1               5                  10                  15

Tyr Ala Leu Ile Phe Gly Met Phe Gly Ile Val Val Met Val Ile Glu
            20                  25                  30

Thr Glu Leu Ser Trp Gly Leu Tyr Ser Lys Asp Ser Met Phe Ser Leu
        35                  40                  45

Ala Leu Cys
    50
```

CHEMICAL COMPOUNDS HAVING ION CHANNEL BLOCKING ACTIVITY FOR THE TREATMENT OF IMMUNE DYSFUNCTION

This application is a continuation of PCT/DK98/00490, filed Nov. 13, 1998.

TECHNICAL FIELD

The present invention relates to chemical compounds having inhibitory activity on an intermediate conductance $Ca^{2+}$ activated potassium channel ($IK_{Ca}$), and the use of such compounds for the treatment or alleviation of diseases or conditions relating to immune dysfunction.

Moreover, the invention relates to a method of screening a chemical compound for inhibitory activity on an intermediate conductance $Ca^{2+}$ activated potassium channel ($IK_{Ca}$).

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Many drugs exert their effects via modulation of ion channels. Examples are anti-epileptic compounds like Phenytoin and Lamotrigine, which block voltage dependent $Na^+$-channels in the brain, anti-hypertensive drugs like Nifedipine and Diltiazem, which block voltage dependent $Ca^{2+}$-channels in smooth muscle cells, and stimulators of insulin release like Glibenclamide and Tolbutamide, which block an ATP-regulated $K^+$-channel in the pancreas.

There is a large and still growing demand for non-toxic immunoregulating agents for use in relation to e.g. organ transplantation and auto-immune diseases.

Some of the currently used immunosuppressive compounds such as Cyclosporin A and FK506 prevent immunological proliferation by inhibition of the $Ca^{2+}$/calmodulin-dependent Ser/Thr phosphatase calcineurin. The usefulness of this class of compounds is limited by their side effects such as renal dysfunction, arterial hypertension, neurological effects (headache, insomnia, tremors, parasthesias, lethargy), gastrointestinal effects (nausea, vomiting, diarrhoea), and diabetes.

Another class of compounds comprising e.g. Azathioprine and Mizorbine interfere in a cytotoxic manner directly with the DNA-replication process. Although cytotoxicity shows some selectivity towards strongly proliferating cells such as activated T- and B-lymphocytes, complications may follow due to effects on dividing cells in the entire body, including bone marrow, hair sacs, the skin, testis, ovary and epithelia such as the airways, the intestinal tract, and the thick ascending limp of the loop of Henle's.

A fairly new approach for suppression of immune responses is to interfere with ion channels in the plasma membrane of cells in the immune system, especially the T- and B-lymphocytes. Upon exposure to antigens by antigen presenting macrophages or to mitogens such as IL-2 or IFN-γ, an initial signal in the switching from the resting phase to the proliferating phase is an activation of the phosphoinositide signalling pathway resulting in an increase in the intracellular concentration of $Ca^{2+}$ ($[Ca^{2+}]_i$) due to $Ca^{2+}$ release from intracellular stores. A sustained elevated $[Ca^{2+}]_i$ is maintained by an increased passive influx through mitogen regulated, voltage-independent Ca-channels. This increase in $[Ca^{2+}]_i$ is vital for the subsequent events leading to cell proliferation and secretion of lymphokines.

In resting T- and B-lymphocytes, the $[Ca^{2+}]$ is approximately $10^7$ fold higher outside versus inside the cell, and the membrane potential is negative inside, i.e. there is an inwardly directed electrochemical $Ca^{2+}$ gradient. Thus, when the Ca-channels are activated they conduct $Ca^{2+}$ into the cell. However, $Ca^{2+}$ influx via the Ca-channels, tends to reduce or even eliminate this gradient, and thus to reduce the influx. Concomitant opening of K-channels keeps the membrane potential negative, and activation of these channels is therefore essential for maintaining a large inwardly directed, electrochemical driving force for $Ca^{2+}$.

In the presence of blockers of lymphocyte K-channels, the cells depolarise, and thereby the $Ca^{2+}$ influx necessary for the activation of the immune response is reduced.

Several types of K-channels have been described in B- and T-lymphocytes including both voltage-dependent K-channels ($K_v$), and voltage-independent $Ca^{2+}$-activated K-channels ($K_{Ca}$). It is well established, that the $K_v$-channels are activated by the $Ca^{2+}$-induced depolarisation of the lymphocyte, and non-selective blockers of $K_v$-channels are therefore quite effective immunosuppressive agents. However, these compounds in general have severe side effects due to block of repolarisation in excitable tissue (seizures, myotonic runs, high blood pressure, etc.).

Considerable effort has been made into the development of immunoselective $K_v$-blockers. The molecular rationale for this, has been the observation that T-lymphocytes express homomeric $K_v$1.3-channels in contrast to excitable cells, which always express several heteromeric subtypes of the $K_v$-channels.

A selective blocker of the $K_v$1.3-homomer might therefore be an ideal, relatively non-toxic, immunosuppressive agent. Initial reports from these pharmacological programs indicate that selective $K_v$1.3-blockers are very effective as anti-inflammatory agents. However, the well-known toxicity of non-selective $K_v$-blockers has apparently not disappeared. An example is the potent $K_v$1.3 blocker CP-339,818. This compound is also a potent blocker of $K_v$1.4, a cardiac and neuronal A-type K-channel. The side-effect of this compound is predicted to be interference with the cardiac action potential (long QT-syndrome toxicity) as well as with the action potential repolarisation and after hyperpolarization in neurons.

SUMMARY OF THE INVENTION

A hitherto untested alternative to the block of the voltage-dependent K-channels is a selective inhibition of the $Ca^{2+}$-activated K-channels in T- and B- lymphocytes. These channels are directly activated by the increased $[Ca^{2+}]_i$ which is the primary signal for lymphocyte activation. Further, contrary to $K_v$-channels, these channels are voltage-independent, and therefore they do not close upon hyperpolarization, implicating that they are even more effective than $K_v$ channels in maintaining a large inward driving force on $Ca^{2+}$ under conditions of elevated intercellular $Ca^{2+}$-concentrations.

Two types of $Ca^{2+}$-activated K-channels have been described from lymphocytes: 1) Small-conductance, apamin-sensitive, $Ca_{2+}$-activated K-channels ($SK_{Ca}$) and 2)⁻ Intermediate-conductance, inwardly rectifying, Clotrimazole-sensitive, $Ca^{2+}$-activated K-channels ($IK_{Ca}$), also referred to as Gardos-channels. Resting T-lymphocytes express both $SK_{Ca}$ and $IK_{Ca}$, whereas B-lymphocytes only express $IK_{Ca}$.

Upon activation, prior to cell proliferation, the expression level of $IK_{Ca}$ increases approximately 30 fold in both T- and B-lymphocytes. The expression levels of both $K_v1.3$ and $SK_{Ca}$ remain unchanged, indicating a major role for the $IK_{Ca}$-channel in induction of T- and B-cell proliferation. Contrary to the $SK_{Ca}$-channels, which are extensively expressed in CNS and heart (measured as mRNA abundance by Northern hybridisation) and in PNS, skeletal muscle, hepatocytes (measured as functional channels by electrophysiology), expression of $IK_{Ca}$-channels have never been reported from any excitable tissue. In fact, blood cells such as erythrocytes, monocytes, lymphocytes, endothelial cells, and certain cell-lines with an epithelial ancestry, Ehrlich ascites tumor cells and HeLa cells appear to be the main source of this type of channels.

Furthermore, the very recent cloning of $IK_{Ca}$ has enabled the demonstration of the mRNA for this gene in several organs including placenta, salivary glands, lung and pancreas. Thus, specific blockers of $IK_{Ca}$ are likely to be very effective as immunosuppressive agents, and devoid of side effects on excitable tissue. In fact, the $IK_{Ca}$-inhibitor Clotrimazole (which is also a blocker of the cytochrome P-450 system) has been extensively used clinically in the systemic treatment of fungal infections. No toxicity related to K-channel blockade has been described.

Accordingly, in its first aspect, the invention relates to the use of a chemical compound having $IK_{Ca}$ inhibitory activity for the manufacture of a medicament for the treatment or alleviation of diseases, disorders or. conditions relating to immune dysfunction.

In another aspect the invention provides a pharmaceutical compositions for use in the treatment or alleviation of diseases, disorders or conditions relating to immune dysfunction, comprising an effective amount of a chemical compound having $IK_{Ca}$ inhibitory activity.

In yet another aspect the invention provides a method of screening a chemical compound for inhibitory activity on an intermediate conductance $Ca^{2+}$ activated potassium channel ($IK_{Ca}$), which method comprises the steps of subjecting an $IK_{Ca}$ containing cell to the action of the chemical compound, and monitoring the membrane potential of the $IK_{Ca}$ containing cell.

DETAILED DISCLOSURE OF THE INVENTION

The present invention relates to the use of a chemical compound having $IK_{Ca}$ inhibitory activity for treatment or alleviation of diseases or conditions relating to immune dysfunction.

Chemical Compound having $IK_{Ca}$ Inhibitory Activity

According to the invention, chemical compound having $IK_{Ca}$ inhibitory activity may be identified by its ability to inhibit hyperpolarization of an $IK_{Ca}$ containing cell, i.e. a cell containing an intermediate conductance $Ca^{2+}$activated potassium channel ($IK_{Ca}$). In a preferred embodiment, the chemical compounds having $IK_{Ca}$ inhibitory activity is identified by the method of screening described below.

Preferred chemical compounds having $IK_{Ca}$ inhibitory activity for use according to the invention are the derivatives of 1,4-dihydropyridine-3,5-dicarboxylic acid, the imidazole derivatives, the triazole derivatives, the nitroimidazole derivatives, and the derivatives and metabolites of Clotrimazole, described below. The derivatives of 1,4-dihydropyridine-3,5-dicarboxylic acid have been disclosed in e.g. U.S. Pat. No. 3,799,934. The imidazole derivatives, the triazole derivatives, and the nitroimidazole derivatives have been disclosed in e.g. U.S. Pat. No. 5,273,992. The derivatives and metabolites of Clotrimazole have been disclosed in e.g. WO 96/08242.

Derivatives of 1,4-dihydropyridine-3,5-dicarboxylic acid

In a preferred embodiment, the chemical compound having $IK_{Ca}$ inhibitory activity for use according to the invention is a symmetric or asymmetric derivative of 1,4-dihydropyridine-3,5-dicarboxylic acid represented by the general formula

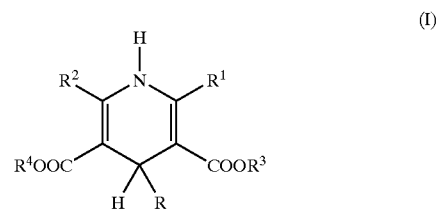

(I)

wherein

R represents an alkyl group or a cycloalkyl group;

or R represents a mono- or polycyclic aryl group, which aryl group may be substituted one or more times with substituents selected from the grgroup consisting of halogen, trifluoromethyl (—$CF_3$), nitro (—$NO_2$), cyano (—CN), azido (—$N_3$), a group of the formula —S(O)$_n$-alkyl, —S(O)$_n$—NH-alkyl, or —S(O)$_n$—N-(alkyl)$_2$, in which n has a value of 0, 1 or 2, an alkyl group, a cycloalkyl group, an alkoxy group, a trifluoromethyl-oxy group (—$OCF_3$), a carboxy group (—COOH), a group of the formula —COO-alkyl, a carbamoyl group (—$CONH_2$), and a group of the formula —CONH-alkyl or —CON(alkyl)$_2$;

or R represents a mono- or poly-heterocyclic group, which heterocyclic group may be substituted one or more times with alkyl, alkoxy, a carboxy group (—COOH), a group of the formula —COO-alkyl, and/or a group of the formula —COO-phenyl;

and $R^1$, $R^2$, $R^3$ and $R^4$, independent of each another, represents hydrogen, an alkyl group, a cycloalkyl group, an alkenyl group, an alkynyl group, an alkoxy group, a phenyl group, a phenyl-alkyl group, a furanyl group, a furanyl-alkyl group, a pyridyl group, or a pyridyl-alkyl group;

or a pharmaceutically acceptable acid addition salt thereof.

In a more preferred embodiment, the chemical compound for use according to the invention is a compound of the general formula (I) in which R represents a cyclohexyl group; or R represents a monosubstituted phenyl group, which phenyl group may be substituted one or more times with substituents selected from the group consisting of halogen, trifluoromethyl (—$CF_3$), nitro (—$NO_2$), and cyano (—CN); or R represents a pyridyl group or a dihydro-pyridyl group, which groups may be monosubstituted with a group of the formula —COO-alkyl, or a group of the formula—COO-phenyl.

In a another preferred embodiment, the chemical compound for use according to the invention is a compound of the general formula (I) in which R represents a 2-nitrophenyl group, a 3-nitrophenyl group, a 4-nitrophenyl group, a 2-trifluoromethylphenyl group, a 3-trifruoromethylphenyl group, or a 4-trifruoromethylphenyl group; a 2-cyanophenyl group, a 3-cyanophenyl group, a 4-cyanophenyl group; or R represents a 2-pyridyl, a 3-pyridyl or a 4-pyridyl group, a 1,2-, 1,4- or 1,6-dihydro-2-pyridyl, a 1,2-, 1,4- or 1,6-dihydro-3-pyridyl, or a 1,2- or 1,4-dihydro-4-pyridyl group, which pyridyl or dihydropyridyl groups may be monosubstituted with $C_{1-6}$-alkyl, a group of the formula —COO—$C_{1-6}$-alkyl, or a group of the formula —COO-phenyl.

In yet another preferred embodiment, the chemical compound for use according to the invention is a compound of the general formula (I) in which $R^1$, $R^2$, $R^3$ and $R^4$, independent of each another, represents $C_{1-6}$-alkyl, preferably methyl, ethyl, propyl, isopropyl, butyl, or isobutyl.

In a more preferred embodiment, the chemical compound for use according to the invention is a compound of the general formula (I) which is an asymmetric derivative of the 1,4-dihydropyridine-3,5-dicarboxylic acid represented by the general formula (I). Preferred asymmetric derivatives includes asymmetric $C_{1-6}$-alkyl derivatives of the 1,4-dihydropyridine-3,5-dicarboxylic acid represented by the general formula (I). Most preferred asymmetric compounds include 1,4-dihydro-2,6-dimethyl-4-(2-nitrophenyl)pyridine-3,5-dicarboxylic acid ethyl methyl ester;
1,4-dihydro-2,6-dimethyl-4-(2-nitrophenyl)pyridine-3,5-dicarboxylic acid propyl methyl ester;
1,4-dihydro-2,6-dimethyl-4-(2-nitrophenyl)pyridine-3,5-dicarboxylic acid isopropyl methyl ester;
1,4-dihydro-2,6-dimethyl-4-(3-nitrophenyl)pyridine-3,5-dicarboxylic acid ethyl methyl ester (Nitrendipine);
1,4-dihydro-2,6-dimethyl-4-(3-nitrophenyl)pyridine-3,5-dicarboxylic acid propyl methyl ester;
1,4-dihydro-2,6-dimethyl-4-(3-nitrophenyl)pyridine-3,5-dicarboxylic acid isopropyl methyl ester;
1,4-dihydro-2,6-dimethyl-4-(4-nitrophenyl)pyridine-3,5-dicarboxylic acid ethyl methyl ester;
1,4-dihydro-2,6-dimethyl-4-(4-nitrophenyl)pyridine-3,5-dicarboxylic acid propyl methyl ester;
1,4-dihydro-2,6-dimethyl-4-(4-nitrophenyl)pyridine-3,5-dicarboxylic acid isopropyl methyl ester;
1,4-dihydro-2,6-dimethyl-4-(2-trifluorophenyl)pyrdine-3,5-dicarboxylic acid ethyl methyl ester;
1,4-dihydro-2,6-dimethyl-4-(2-trifluorophenyl)pyridine-3,5-dicarboxylic acid propyl methyl ester;
1,4-dihydro-2,6-dimethyl-4-(2-trifluorophenyl)pyridine-3,5-dicarboxylic acid isopropyl methyl ester;
1,4-dihydro-2,6-dimethyl-4-(3-trifluorophenyl)pyridine-3,5-dicarboxylic acid ethyl methyl ester;
1,4-dihydro-2,6-dimethyl-4-(3-trifluorophenyl)pyridine-3,5-dicarboxylic acid propyl methyl ester;
1,4-dihydro-2,6-dimethyl-4-(3-trifluorophenyl)pyridine-3,5-dicarboxylic acid isopropyl methyl ester;
1,4-dihydro-2,6-dimethyl-4-(4-trifluorophenyl)pyridine-3,5-dicarboxylic acid ethyl methyl ester;
1,4-dihydro-2,6-dimethyl-4-(4-trifluorophenyl)pyridine-3,5-dicarboxylic acid propyl methyl ester;
1,4-dihydro-2,6-dimethyl-4-(4-trifluorophenyl)pyridine-3,5-dicarboxylic acid isopropyl methyl ester;
1,4-dihydro-2,6-dimethyl-4-(2-cyanophenyl)pyridine-3,5-dicarboxylic acid ethyl methyl ester;
1,4-dihydro-2,6-dimethyl-4-(2-cyanophenyl)pyridine-3,5-dicarboxylic acid propyl methyl ester;
1,4-dihydro-2,6-dimethyl-4-(2-cyanophenyl)pyridine-3,5-dicarboxylic acid isopropyl methyl ester;
1,4-dihydro-2,6-dimethyl-4-(3-cyanophenyl)pyridine-3,5-dicarboxylic acid ethyl methyl ester;
1,4-dihydro-2,6-dimethyl-4-(3-cyanophenyl)pyridine-3,5-dicarboxylic acid propyl methyl ester;
1,4-dihydro-2,6-dimethyl-4-(3-cyanophenyl)pyridine-3,5-dicarboxylic acid isopropyl methyl ester;
1,4-dihydro-2,6-dimethyl-4-(4-cyanophenyl)pyridine-3,5-dicarboxylic acid ethyl methyl ester;
1,4-dihydro-2,6-dimethyl-4-(4-cyanophenyl)pyridine-3,5-dicarboxylic acid propyl methyl ester;
1,4-dihydro-2,6-dimethyl-4-(4-cyanophenyl)pyridine-3,5-dicarboxylic acid isopropyl methyl ester;
1,4-dihydro-2,6-dimethyl-4-(2-pyridyl)pyridine-3,5-dicarboxylic acid ethyl methyl ester;
1,4-dihydro-2,6-dimethyl-4-(2-pyridyl)pyridine-3,5-dicarboxylic acid propyl methyl ester;
1,4-dihydro-2,6-dimethyl-4-(2-pyridyl)pyridine-3,5-dicarboxylic acid isopropyl methyl ester;
1,4-dihydro-2,6-dimethyl-4-(3-pyridyl)pyridine-3,5-dicarboxylic acid ethyl methyl ester;
1,4-dihydro-2,6-dimethyl-4-(3-pyridyl)pyridine-3,5-dicarboxylic acid propyl methyl ester;
1,4-dihydro-2,6-dimethyl-4-(3-pyridyl)pyridine-3,5-dicarboxylic acid isopropyl methyl ester;
1,4-dihydro-2,6-dimethyl-4-(4-pyridyl)pyridine-3,5-dicarboxylic acid ethyl methyl ester;
1,4-dihydro-2,6-dimethyl-4-(4-pyridyl)pyridine-3,5-dicarboxylic acid propyl methyl ester; and
1,4-dihydro-2,6-dimethyl-4-(4-pyridyl)pyridine-3,5-dicarboxylic acid isopropyl methyl ester.

In another preferred embodiment, the chemical compound is a symmetric derivative of 1,4-dihydropyridine-3,5-dicarboxylic acid represented by the general formula (I). Preferred chemical compounds include the symmetric $C_{1-6}$-alkyl derivatives of the 1,4-dihydropyridine-3,5-dicarboxylic acid. Most preferred symmetric chemical compounds for use-according to the invention include 1,4-dihydro-2,6-dimethyl-4-(2-nitrophenyl)pyridine-3,5-dicarboxylic acid dimethyl ester (Nifedipine);
1,4-dihydro-2,6-dimethyl-4-(2-nitrophenyl)pyridine-3,5-dicarboxylic acid diethyl ester;
1,4-dihydro-2,6-dimethyl-4-(3-nitrophenyl)pyridine-3,5-dicarboxylic acid dimethyl ester;
1,4-dihydro-2,6-dimethyl-4-(3-nitrophenyl)pyridine-3,5-dicarboxylic acid diethyl ester;
1,4-dihydro-2,6-dimethyl-4-(4-nitrophenyl)pyridine-3,5-dicarboxylic acid dimethyl ester;
1,4-dihydro-2,6-dimethyl-4-(4-nitrophenyl)pyridine-3,5-dicarboxylic acid diethyl ester;
1,4-dihydro-2,6-dimethyl-4-(2-trifluorophenyl)pyridine-3,5-dicarboxylic acid dimethyl ester;
1,4-dihydro-2,6-dimethyl-4-(2-trifluorophenyl)pyridine-3,5-dicarboxylic acid diethyl ester;
1,4-dihydro-2,6-dimethyl-4-(3-trifluorophenyl)pyridine-3,5-dicarboxylic acid dimethyl ester;
1,4-dihydro-2,6-dimethyl-4-(3-trifluorophenyl)pyridine-3,5-dicarboxylic acid diethyl ester;
1,4-dihydro-2,6-dimethyl-4-(4-trifluorophenyl)pyridine-3,5-dicarboxylic acid dimethyl ester;
1,4-dihydro-2,6-dimethyl-4-(4-trifluorophenyl)pyridine-3,5-dicarboxylic acid diethyl ester;
1,4-dihydro-2,6-dimethyl-4-(2-cyanophenyl)pyridine-3,5-dicarboxylic acid dimethyl ester;
1,4-dihydro-2,6-dimethyl-4-(2-cyanophenyl)pyridine-3,5-dicarboxylic acid diethyl ester;
1,4-dihydro-2,6-dimethyl-4-(3-cyanophenyl)pyridine-3,5-dicarboxylic acid dimethyl ester;
1,4-dihydro-2,6-dimethyl-4-(3-cyanophenyl)pyridine-3,5-dicarboxylic acid diethyl ester;
1,4-dihydro-2,6-dimethyl-4-(4-cyanophenyl)pyridine-3,5-dicarboxylic acid dimethyl ester;
1,4-dihydro-2,6-dimethyl-4-(4-cyanophenyl)pyridine-3,5-dicarboxylic acid diethyl ester;
1,4-dihydro-2,6-dimethyl-4-(2-pyridyl)pyridine-3,5-dicarboxylic acid dimethyl ester;

1,4-dihydro-2,6-dimethyl-4-(2-pyridyl)pyridine-3,5-dicarboxylic acid diethyl ester;
1,4-dihydro-2,6-dimethyl-4-(3-pyridyl)pyridine-3,5-dicarboxylic acid dimethyl ester;
1,4-dihydro-2,6-dimethyl-4-(3-pyridyl)pyridine-3,5-dicarboxylic acid diethyl ester;
1,4-dihydro-2,6-dimethyl-4-(4-pyridyl)pyridine-3,5-dicarboxylic acid dimethyl ester;
1,4-dihydro-2,6-dimethyl-4-(4-pyridyl)pyridine-3,5-dicarboxylic acid diethyl ester;
1,4-dihydro-2,6-dimethyl-4-cyclohexylpyridine-3,5-dicarboxylic acid dimethyl ester; and
1,4-dihydro-2,6-dimethyl-4-cyclohexylpyridine-3,5-dicarboxylic acid diethyl ester.

Imidazole Derivatives

In another preferred embodiment, the chemical compound having $IK_{Ca}$ inhibitory activity for use according to the invention is an imidazole derivative selected from the group consisting of
1-[(2-chlorophenyl)-diphenyl-methyl]-1H-imidazole (Clotrimazole);
1-[(3-chlorophenyl)-diphenyl-methyl]-1H-imidazole;
1-[(4-chlorophenyl)-diphenyl-methyl]-1H-imidazole;
1-[(2-chlorophenyl)-(4-hydroxyphenyl)-phenyl-methyl]-1H-imidazole;
1-[(3-chlorophenyl)-(4-hydroxyphenyl)-phenyl-methyl]-1H-imidazole;
1-[(4-chlorophenyl)-(4-hydroxyphenyl)-phenyl-methyl]-1H-imidazole;
1-[2-(2,4-dichlorophenyl)-2-[(2,4-dichlorophenyl)methoxy]-1H-imidazole (Miconazole);
1-Acetyl-4[4-[[2-(2,4-dichlorophenyl)-2-(1H-imidazol-1-ylmethyl)-1,3-dioxolan-4yl]methoxy]phenyl]piperazine (Ketoconazole);
1-[2-[(4-chlorophenyl)methoxyl]-2-(2,4-dichlorophenyl)ethyl]-1H-imidacole (Econazole);
1-[4-(4-chlorophenyl)-2-(2,6-dichlorophenylthio)butyl] imidazole mononitrate (Butoconazole);
2',4'-dichloro-2-imidazol-1-ylacetophenone-(Z)-O-(2,4-dichlorobenzyl)oxime mononitrate (Oxiconazole);
1-[2,4-dichloro-β-(4-chlorobenzyl)thiophenethyl]imidazole nitrate (Sulconazole); and
1-[2-[(2-chloro-3-thienyl)methoxy]-2-(2,4-dichlorophenyl)ethyl]-1H-imidazole (Thioconazole).

Triazole Derivatives

In a third preferred embodiment, the chemical compound having $IK_{Ca}$ inhibitory activity for use according to the invention is a triazole derivative selected from the group consisting of
2-(2,4-difluorophenyl)-1,3-bis(1H-1,2,4-triazol-1-yl) propan-2-ol (Fluconazole);
1-{4-[[2-(2,4-dichlorophenyl)r-2-(1H-1,2,4-triazol-1-ylmethyl)-1,3-dioxolan-c-4-yl]methoxy]-phenyl}-4-isopropylpiperazine (Terconazole);
(±)-2-sec-butyl-4-[4-(4-{4-[(2R*,4S*)-2-(2,4-dichlorophenyl)-2-(1H-1,2,4-triazol-1ylmethyl)-1,3-dioxolan-4-ylmethoxy]phenyl}-piperazin-1-yl)phenyl]-2,4-dihydro-1,2,4-triazol-3-one (Itraconazole).

Nitroimidazole Derivatives

In a fourth preferred embodiment, the chemical compound having $IK_{Ca}$ inhibitory activity for use according to the invention is a nitroimidazole derivative selected from the group consisting of
2-methyl-5-nitroimidazole-1-ethanol (Metronidazole);
1-[2-(ethylsulphonyl)ethyl]-2-methyl-5-nitroimidazole (Tinidazole);
4-[2-(5-nitroimidazol-1-yl)ethyl]morpholine (Nimorazole);
1-chloro-3-(2-methyl-5-nitroimidazol-1-yl)propan-2-ol (Omidazole), and
N-benzyl-2-(2-nitroimidazol-1-yl)acetamide (Benznidazole).

Metabolites of Clotrimazole

In yet another preferred embodiment chemical compounds having $IK_{Ca}$ inhibitory activity for use according to the invention are derivatives and metabolites of Clotrimazole, as described in WO 96/08242.

The derivatives and metabolites of Clotrimazole for use according to the invention may be characterised by the following general formula

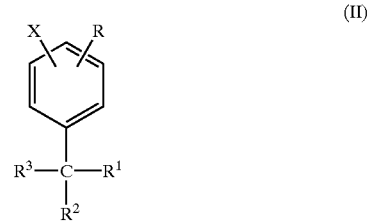

(II)

wherein
X represents halogen, a trifluoromethyl group, a nitro group, or a cyano group;
R represents hydrogen, halogen, hydroxy, an alkyl group, a cycloalkyl group, an alkoxy group, or an alkyloxy group;
$R^1$ represents hydrogen, or a phenyl group, which phenyl group may be substituted one or more times with substituents selected from the group consisting of halogen and hydroxy;
$R^2$ represents hydrogen, hydroxyl, alkyl, alkoxy;
$R^3$ represents a group of the formula —Y—CH$_2$—R$^5$, wherein Y represents oxygen (—O—) or sulphur (—S—); a group of the formula =NO—CH$_2$R$^5$; a group of the formula —O-phenyl—CH=CH$_2$; a group of the formula —CH$_2$—CH(CH$_3$)—S-phenyl, which phenyl may be substituted one or more times with substituents selected from the group consisting of halogen and hydroxy; or a phenyl group, which phenyl may be substituted one or more times with substituents selected from the group consisting of halogen and hydroxy; and wherein R$^5$ represents an ethenyl group (CH$_2$=CH—); a phenyl group, which phenyl may be substituted one or more times with substituents selected from the group consisting of halogen and hydroxy; a phenyl-S-phenyl group, a group of the formula CH2—O-phenyl, which phenyl may be substituted one or more times with substituents selected from the group consisting of halogen and hydroxy; or a group of the formula

(III)

wherein Z represents S, O or N;
and R$^6$ represents hydrogen, halogen or hydroxy;
or a pharmaceutically acceptable acid addition salt thereof.

Preferred derivatives and metabolites for use according to the invention include 2-chlorophenyl-4-hydroxyphenyl-phenyl-methane;
2-chlorophenyl-bis-phenyl-methane;
2-chlorophenyl-bis-phenyl-methanol;
3-(1-[2,4-dichlorophenyl]-ethoxymethyl)-2-chlorothiophene;
0-(2,4-dichlorobenzyl)-2,4-dichloroacetophenone oxime;
1-(2,4-dichloro)-1-(4-(phenylthio)benzyloxy)ethane;
1-(2,4-dichlorophenyl) 1-1(allyloxy)ethane;
1-(2,4-dichlorophenyl)-1-(4-chlorobenzylthio)ethane;
1-(2,4-dichlorophenyl)-1-(2,4-dichlorobenzyloxy)ethane;
1-(2,4-dichlorophenyl)ethyl-2,6-dichlorobenzyl ether;
1-(2-[4-chlorophenoxy]ethyloxy)-1-(2,4-dichlorophenyl) propene;
1-(2,4-dichlorophenyl)-ethyl-(4-chlorophenyl)methyl ether;
3-chlorobenzyl-2-vinylphenyl ether; and
1-(4-chlorophenyl)-3-(2,6-dichlorophenylthio)butane.

Definition of Substituents

In the context of this invention halogen represents a fluorine, a chlorine, a bromine or a iodine atom.

In the context of this invention an alkyl group designates a univalent saturated, straight or branched hydrocarbon chain. The hydrocarbon chain preferably contain of from one to eighteen carbon atoms ($C_{1-8}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a most preferred embodiment alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention an alkoxy group designates an "alkyl-O—" group, wherein alkyl is as defined above.

In the context of this invention a mono- or polycyclic aryl group designates a monocyclic or polycyclic aromatic hydrocarbon group. Examples of preferred aryl groups of the invention are phenyl, naphthyl and anthracenyl.

In the context of this invention a mono- or polyheterocyclic group is a mono- or polycyclic aromatic group, which holds one or more heteroatoms in its ring structure. Preferred heterocyclic monocyclic groups of the invention are 5- and 6 membered heterocyclic monocyclic groups. Examples of preferred heterocyclic monocyclic groups of the invention include furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolyl, pyridazinyl, pyridyl, pyrimidinyl, pyrrolyl, thiadiazolyl, thiazolyl, and thienyl. Examples of preferred heterocyclic polycyclic groups of the invention include benzimidazolyl, indolyl, isoquinolyl and quinolyl.

The chemical compounds for use according to the invention have been described and may be prepared by methods known in the art.

Pharmaceutically Acceptable Salts

The chemical compound of the invention may be provided in any form suitable for the intended administration. Suitable forms include pharmaceutically (i.e. physiologically) acceptable salts, or pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acids the sulphate derived from sulphuric acid, the tartrate derived from tartaric acid, the toluene-p-sulphonate derived from p-toluene sulfonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt, of a chemical compound of the invention containing a carboxy group.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Method of Screening

In another aspect, the present invention provides a method for the screening of chemical compounds for inhibitory activity on an intermediate conductance $Ca^{2+}$ activated potassium channel ($IK_{Ca}$), by which method a chemical compound having $IK_{Ca}$ inhibitory activity is identified by its ability to inhibit hyperpolarization of the cell.

The screening method of the invention comprises the steps of subjecting an $IK_{Ca}$ containing cell to the action of the chemical compound to be screened, and monitoring the membrane potential of the $IK_{Ca}$ containing cell.

More particularly the monitoring of the membrane potential of the $IK_{Ca}$ containing cell of step (ii) is carried out in order to monitor changes in the membrane potential caused by the action of the chemical compound.

The $IK_{Ca}$ Containing Cell

The $IK_{Ca}$ used in the method of the invention may be of any origin, however, preferably of human or animal origin. Also, the $IK_{Ca}$ may be endogenous or it may be exogenous to the cell in question.

In a preferred embodiment, the $IK_{Ca}$ of the $IK_{Ca}$ containing cell is an ion channel that is endogenous to the cell in question, and which cell may in particular be a T- or B-lymphocyte or other cells known to express $IK_{Ca}$, e.g. a HeLa cell, or a cell of epithelial origin, a cell of endothelial origin, or a blood cell.

In another preferred embodiment, the $IK_{Ca}$ of the $IK_{Ca}$ containing cell is an ion channel that is exogenous to the cell in question, and which cell may in particular be a human embryonic kidney (HEK) cell, a HEK 293 cell, a Chinese hamster ovary (CHO) cell, a Xenopus laevis oocyte (XLO) cell, or any other cell line able to express $IK_{Ca}$.

The $IK_{Ca}$ preferably is of human origin. In particular the $IK_{Ca}$ may be isolated from salivary glands, from lung tissue, from tracheal tissue, from placenta tissue, from pancreas tissue, from lymphocytes, from colon tissue, from kidney tissue, from thymus tissue, from bone marrow, from prostate tissue, from stomach tissue, from liver tissue, from foetal liver tissue, from mammary glands, from small intestine tissue, from spleen tissue, or from lymph node tissue. Preferably the $IK_{Ca}$ may be isolated from salivary glands, from lung tissue, from tracheal tissue, from placenta tissue, from pancreas tissue, or from lymphocytes.

In a most preferred embodiment, the $IK_{Ca}$ is encoded by the DNA sequence presented as SEQ ID NO: 1, or a homologous sequence, e.g. a DNA sequence showing a homology to SEQ ID NO: 1 of at least 80%, more preferred at least 90%, most preferred at least 95%.

Monitoring of the Membrane Potential

According to the method of the invention the membrane potential is monitored in order to determine changes in the membrane potential. The membrane potential may be monitored using established methods.

In a preferred embodiment monitoring of the membrane potential of the $IK_{Ca}$ containing cell is performed by patch clamp techniques, e.g. as described by Hamill, O. P., et al., *Pflügers Arch.* 1981 351 85–100. In a more preferred embodiment, monitoring of the membrane potential of the $IK_{Ca}$ containing cell is performed by the automatic patch clamp method described in pending patent application DK 1151/97.

In another preferred embodiment monitoring of the membrane potential of the $IK_{Ca}$ containing cell is performed using fluorescence methods.

In a preferred method of the invention, the $IK_{Ca}$ containing cell is mixed with a membrane potential indicating agent, that allow for a determination of changes in the membrane potential of the cell, caused by the addition of the test compound.

The membrane potential indicating agent employed in the method of the invention may be any agent that allow monitoring of changes in the membrane potential. In a preferred embodiment, the membrane potential indicating agent is a fluorescent indicator. The fluorescent indicator must be sufficiently sensitive so as to produce a detectable change in fluorescence intensity in the presence of calcium ions.

Preferred fluorescent indicators are in particular $DIBAC_4(3)$, $DiOC5(3)$, and $DIOC2(3)$.

Monitoring of the membrane potential of the $IK_{Ca}$ containing cell may then be performed by spectroscopic methods, e.g. using a FLIPR assay (Fluorescence Image Plate Reader; available from Molecular Devices), or by using the automated analysis equipment described in U.S, Pat. No. 5,670,113.

In a separate aspect the invention relates to an encompasses the chemical compounds identified by the method of the invention and their use the use of these compounds for the treatment or alleviation of diseases or conditions relating to immune dysfunction.

Biological Activity

As described above, the $IK_{Ca}$ inhibitory compounds of the invention are useful as immune modulating agents, i.e. agents capable of regulating the immune system. More particularly, the $IK_{Ca}$ inhibitory compounds of the present invention may be used for reducing or inhibiting undesired immunoregulatory actions.

In a preferred embodiment, the invention relates to the use of an $IK_{Ca}$ inhibitory compound for the treatment or alleviation of a diseases, disorders or condition related to immune dysfunction.

Conditions which may benefit from this treatment include, but are not limited to diseases, disorders or conditions such as autoimmune diseases, e.g. Addison's disease, alopecia areata, Ankylosing spondylitis, hemolytic anemia (anemia haemolytica), pernicious anemia (anemia perniciosa), aphthae, aphthous stomatitis, arthritis, osteoarthritis, rheumatoid arthritis, aspermiogenese, asthma bronchiale, autoimmune asthma, autoimmune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's hyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

Accordingly, in further embodiments, the invention relates to a chemical compound having $IK_{Ca}$ inhibitory activity for use as a medicament.

More specifically the invention relates to the use of a chemical compound having $IK_{Ca}$ inhibitory activity for use in the manufacture of a medicament for the treatment of treatment of diseases related to immune dysfunction. In a preferred embodiment the medicament is an immune system suppressing medicament (an immunosuppressivum).

Pharmaceutical Compositions

In yet another aspect the invention relates to pharmaceutical compositions for use in the treatment or alleviation of diseases, disorders or conditions related to immune dysfunction, which pharmaceutical composition comprises a therapeutically effective amount of a chemical compound having $IK_{Ca}$ inhibitory activity, as identified by the method of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg i.v., and from about 1 $\mu$g/kg to about 100 mg/kg p.o.

In a preferred embodiment, the pharmaceutical composition of the invention comprises a chemical compound which is an imidazole derivative, in particular Clotrimazole, Miconazole, Ketonazole, Econazole, Butoconazole, Oxiconazole, Sulconazole, or Tioconazole.

In another preferred embodiment, the pharmaceutical composition of the invention comprises a chemical compound which is a nitroimidazole derivative, in particular Metronidazole, Tinidazole, Nimorazole, Ornidazole, or Benznidazole.

In yet another preferred embodiment, the pharmaceutical composition of the invention comprises a chemical compound which is a triazole derivative, in particular Fluconazole, Tercolazole, or Itraconazole.

In a further preferred embodiment, the pharmaceutical composition of the invention comprises a chemical compound which is a metabolite of Clotrimazole, in particular 2-chlorophenyl-4-hydroxy-phenyl-phenyl-methane, 2-chlorophenyl-bis-phenyl-methane, or 2-chlorophenyl-bis-phenyl-methanol.

Method of Treatment

The $IK_{Ca}$ inhibitory compounds of the invention are useful as immune modulating agents, i.e. agents capable of regulating the immune system, and may be used in a method of for reducing or inhibiting undesired immunoregulatory actions.

Therefore, in a separate aspect, the invention relates to a method of treatment or alleviation of diseases, disorders or conditions relating to immune dysfunction in a living body, said method comprising administering to said living body an effective amount of a chemical compound having $IK_{Ca}$ inhibitory activity.

EXAMPLES

The invention is further illustrated with reference to the following examples which are not intended to be in any way limiting to the scope of the invention as claimed.

Example 1
Isolation of a cDNA Encoding Human Placenta $Ca^{2+}$-activated, Intermediate Conductance Potassium Channel Protein The full length coding sequence of a cDNA encoding human placenta $Ca^{2+}$-activated, intermediate conductance potassium channel protein (SEQ ID NO: 2) is radio labelled by random priming and used as a hybridisation probe to screen a human placenta cDNA library under hybridisation conditions of 1 M NaCl, 1% SDS and 50% formamide at 42° C. Hybridisation wash conditions are 55° C., 0.2×SSC and 0.1% SDS. Positively hybridising clones are purified and the nucleotide and predicted amino acid sequence are determined.

Example 2
Assay for DNA Encoding $Ca^{2+}$-activated, Intermediate Conductance Potassium Channel Protein The presence of DNA encoding human placenta $Ca^{2+}$-activated, intermediate conductance potassium channel protein was determined by transfecting mammalian cells with a cDNA preparation and using the membrane patch clamp technique [Hamill, O. P., et al., Pflügers Arch. 1981 351 85–100] or using the Fluorescence Image Plate Reader (FLIPR) assay.

A cDNA encoding the human placenta $Ca^{2+}$-activated, intermediate conductance potassium channel protein was identified by a BLAST search of the expressed sequence tag (EST) database using the query sequence (51 Amino acids):

LGHRRALFEKRKRLSDYALIFGMFGIV-
VMVIETELSWGLYSKDSMFSLALC     (SEQ ID NO: 3), and allowing for mismatches.

A BLAST search retrieved the GenBank Entry No. N56819, a cDNA encoding the entire $Ca^{2+}$-activated, intermediate conductance potassium channel protein.

HEK293 or CHO tissue culture cells were grown in DMEM (Dulbecco's Modified Eagle Medium) supplemented with 10% FCS (foetal calf serum) at 37° C. in 5% $CO_2$. One day prior to transfection, $10^6$ cells were plated in a cell culture T25 flask. The following day, cells were transfected using lipofection (20 µL Lipofectamin™, Life Technologies, with 2.5 µg of the plasmid pNS2Z_hIK2 in a total volume of 540 µL).

Two different plasmids were used for transfection. Cells prepared for the electrophysiological screening were transfected with pNS2Z_hIK2, which besides coding for the human placenta $Ca^{2+}$-activated intermediate conductance potassium channel protein also codes for the green fluorescent protein EGFP. Cells prepared for the FLIPR assay were transfected with pNS1Z_hIK2, which is an analogue to pNS2Z_hIK2 but without the cDNA encoding EGFP. The lipofection mixture was overlaid on the cells and incubated at 37° C. for 5 hours. The cells were then rinsed with regular media and plated either to 30 mm culture dishes (eletrophysiological assay) or to 96-well microtiter plates (FLIPR assay).

18–48 hours after transfection cells were assayed for the presence of $Ca^{2+}$-activated, intermediate conductance potassium channel protein.

Transfected HEK293 cells were assayed for the presence of $Ca^{2+}$-activated, intermediate conductance potassium channel protein by a fluometric technique based on the membrane potential sensitive dye $DIBAC_4(3)$. After transfection, cells were washed twice with a 5 µM $DIBAC_4$(3)/FLIPR buffer solution (100 µl in each well). The FLIPR buffer solution contained in mM: 145 NaCl, 1 KCl, 1 $CaCl_2$, 1 $MgCl_2$, 10 HEPES, 10 glucose and with pH adjusted to 7.4. After the cell wash 180 µl $DIBAC_4$(3)/FLIPR buffer solution was added to each well and the microtiter plate was equilibrated at 35° C. for 20–30 min. A drugplate containing Ionomycin and Thapsigargin was made 10× concentrated and was also equilibrated at 35° C. before starting the experiment.

The FLIPR was programmed to do a sample reading every 20 sec. for a total period of 10 min. The assay was started with a pre-run for 1 min, followed by a simultaneous addition of 20 µl "drug" to all 96 wells. Addition of Ionomycin and Thapsigargin both result in an increase in the intracellular $Ca^{2+}$ concentration, which in turn activated the intermediate conductance potassium channels. This activation was observed as a decrease in the fluorescent signal which correlates to a membrane hyperpolarization.

Example 3
Assays for DNA Encoding $Ca^{2+}$-activated, Intermediate Conductance Potassium Channel Protein.

HEK293 or CHO tissue culture cells were grown in DMEM (Dulbecco's Modified Eagle Medium) supplemented with 10% FCS (foetal calf serum) at 37° C. in 5% $CO_2$. One day prior to transfection, $10^6$ cells were plated in a cell culture T25 flask. The following day, cells were transfected using lipofection (20 µL Lipofectamin™, Life Technologies, with 2.5 µg of the plasmid pNS2Z_hIK2 in a total volume of 540 µL). The lipofection mixture was overlaid on the cells and incubated at 37° C. for 5 hours.

The cells were then rinsed with regular media and plated to a 30 mm culture dish. 18–48 hours after, transfected cells were assayed for the presence of $Ca^{2+}$-activated, intermediate conductance potassium channel protein by electrophysiological measurements.

The presence of DNA encoding human placenta $Ca^{2+}$-activated, intermediate conductance potassium channel protein was determined by transfecting mammalian cells with a cDNA preparation and by using the patch clamp technique (see Hamill O P et al., Pflüagers Arch. 1981 351 85–100).

Whole cell currents were recorded using a pipette solution of 144 mM KCl, 1 mM EGTA, 9 mM NTA, 1.085 mM $CaCl_2$, 5.54 mM $MgCl_2$, and 10 mM HEPES (pH 7.2) and a bath solution of 144 mM KCl, 2 mM $CaCl_2$, 1 mM $MgCl_2$, 0.01% (w/v) BSA and 10 mM HEPES (pH=7.4). Current traces were recorded from cells containing human $Ca^{2+}$-activated, intermediate conductance potassium channels after application of voltage ramps (−100 mV to +100 mV, 200 ms duration).

Clotrimazole sensitivity of the expressed channels was determined by addition of 1 µM Clotrimazole to the bath solution. Application of Clotrimazole resulted in an inhibition of the $Ca^{2+}$-activated potassium current which was reversed by washout of Clotrimazole from the bath solution.

An $IC_{50}$ value of 153 nM for Clotrimazole was calculated from the kinetics of the block.

Example 4
Inhibition of T Cell Proliferation

The chemical compounds used according to the invention prevent immunological proliferation by selective inhibition of the $Ca^{2+}$-activated K-channels in T- and B-lymphocytes. This effect may be verified using various proliferation assays. In this experiment the proliferative assay described by Ødum et al. [Ødum N, Kanner S B, Ledbetter J A, & Svejgaard A; *J. Immunol.* 1993 150 (12) 5289–5298] was used.

The chemical compounds representative of the invention tested in this experiment are Nitrendipine, a derivative of the 1,4-dihydropyridine-3,5-dicarboxylic acid, and the imidazole derivative Clotrimazole.

Assays were performed in culture medium (RPMI 1640; available from Gibco, Grand island, N.Y.) supplemented with 10% pooled human serum, 2 mM L-glutamine, 100 µg/ml penicillin, and 100 µg/ml streptomycin (available from Novo Nordisk, Copenhagen, Denmark) in 96-well round bottom tissue culture plates (available from Nunc, Roskilde, Denmark) with a final volume of 200 µl.

T cells were preincubated for three hours with the test compounds before addition of antigen (crude Candida albicans extract, 10 µg/ml). T cells were cultured at $5 \times 10^4$ cells/well for 144 hours. Twelve hours before harvest, [$^3$H] thymidine (1× Ci/well) was added. The cells were harvested onto glass fibre filters, and the [$^3$H]thymidine incorporation was measured in a scintillation counter. The results were expressed as mean counts per minute (cpm) from triplicate cultures.

TABLE 1

Inhibition of T Cell Proliferation

| | T Cell Proliferation (cpm × $10^{-3}$) | | | |
|---|---|---|---|---|
| | Medium | Antigen | | |
| | Solvent | 1 µM | 5 µM | 10 µM |
| Clotrimazole | 0.2 | 5.8 | 4.2 | 1.8 |
| Nitrendipine | 0.2 | 5.6 | 3.8 | 4.0 |

These results show that the number of T cells decreases in the presence of increasing concentrations of the chemical compound of the invention, and support the fact that the chemical compounds of the invention inhibit the antigen induced T cell proliferation and thus are useful for the reduction or inhibition of undesired immunoregulatory actions.

What is claimed is:

1. A method for treatment or alleviation of a disease, condition or disorder selected from the group consisting of inflammatory bowel disease, Chron's disease, colitis ulcerosa, Coeliac disease, dermatitis herpetiformis, dermatomyositis, enteritis allergia, erytherma nodosum leprosum, ileitis regionalis, psoriasis, purpura, scleritis or scleroderma, said method comprising administering to a living body in need thereof an effective amount at least one compound selected from the group consisting of
  an imidazole derivative selected from the group consisting of
1-[(2-chlorophenyl)-diphenyl-methyl]-1H-imidazole (Clotrimazole);
1-[(3-chlorophenyl)-diphenyl-methyl]-1H-imidazole;
1-[(4-chlorophenyl)-diphenyl-methyl]-1H-imidazole;
1-[(2-chlorophenyl)-(4-hydroxyphenyl)-phenyl-methyl]-1H-imidazole;
1-[(3-chlorophenyl)-(4-hydroxyphenyl)-phenyl-methyl]-1H-imidazole;
1-[(4-chlorophenyl)-(4-hydroxyphenyl)-phenyl-methyl]-1H-imidazole;
1-[2-(2,4-dichlorophenyl)-2-[(2,4-dichlorophenyl)methoxy]-1H-imidazole (Miconazole);
1-Acetyl-4[4-[(2-(2,4-dichlorophenyl)-2-(1H-imidazol-1-ylmethyl)-1,3-dioxolan-4yl]methoxy]phenyl]piperazine (Ketoconazole);
1-[2-[(4-chlorophenyl)methoxyl]-2-(2,4-dichlorophenyl) ethyl]-1H-imidacole (Econazole);
1-[4-(4-chlorophenyl)-2-(2,6-dichlorophenylthio)butyl] imidazole mononitrate (Butoconazole);
2',4'-dichloro-2-imidazol-1-ylacetophenone-(Z)—O—(2,4-dichlorobenzyl)oxime mononitrate (Oxiconazole);
1-[2,4-dichloro-β-(4-chlorobenzyl)thiophenethyl]imidazole nitrate (Sulconazole); and
  1-[2-[(2-chloro-3-thienyl)methoxy]-2-(2,4-dichlorophenyl)ethyl]-1H-imidazole (Thioconazole);
a triazole derivative selected from the group consisting of
2-(2,4-difluorophenyl)-1,3-bis(1H-1,2,4-triazol-1-yl) propan-2-ol (Fluconazole);
1-{4-[[2-(2,4-dichlorophenyl)r-2-(1H-1,2,4-triazol-1-ylmethyl)-1,3-dioxolan-c-4-yl]methoxy]-phenyl}-4-isopropylpiperazine (Terconazole); and
(±)-2-sec-butyl-4-[4-(4-{4-[(2R*,4S*)-2-(2,4-dichlorophenyl)-2-(1H-1,2,4-triazol-1ylmethyl)-1,3-dioxolan-4-ylmethoxy]phenyl}-piperazin-1-yl)phenyl]-2,4-dihydro-1,2,4-triazol-3-one (Itraconazole); and
a nitroimidazole derivative selected from the group consisting of
2-methyl-5-nitroimidazole-1-ethanol (Metronidazole);
1-[2-(ethylsulphonyl)ethyl]-2-methyl-5-nitroimidazole (Tinidazole);
4-[2-(5-nitroimidazol-1-yl)ethyl]morpholine (Nimorazole);
1-chloro-3-(2-methyl-5-nitroimidazol-1-yl)propan-2-ol (Ornidazole); and
N-benzyl-2-(2-nitroimidazol-1-yl)acetamide (Benznidazole).

2. The method of claim 1, wherein the disease, disorder or condition is dermatitis herpetiformis, dermatomyosis, enteritis allergia, psoriasis, scleritis or scleroderma.

3. The method of claim 2, said method comprising administering to said living body an effective amount of 1-[(2-chlorophenyl)-diphenyl-methyl]-1H-imidazol (Clotrimazole).

4. The method of claim 3, wherein the disease, disorder or condition is psoriasis.

5. A method for treatment or alleviation of a disease, condition or disorder selected from the group consisting of inflammatory bowel disease, Chron's disease, colitis ulcerosa, Coeliac disease, dermatitis herpetiformis, dermatomyositis, enteritis allergia, erytherma nodosum leprosum, ileitis regionalis, psoriasis, purpura, scleritis or scleroderma, said method comprising administering to a living body in need thereof an effective amount of 1,4-dihydropyridine-3,5-dicarboxylic acid derivative selected from the group consisting of 1,4-dihydro-2,6-dimethyl-4-(2-nitrophenyl)pyridine-3,5-dicarboxylic acid ethyl methyl ester;
1,4-dihydro-2,6-dimethyl-4-(2-nitrophenyl)pyridine-3,5-dicarboxylic acid propyl methyl ester;
1,4-dihydro-2,6-dimethyl-4-(2-nitrophenyl)pyridine-3,5-dicarboxylic acid isopropyl methyl ester;
1,4-dihydro-2,6-dimethyl-4-(3-nitrophenyl)pyridine-3,5-dicarboxylic acid ethyl methyl ester (Nitrendipine);
1,4-dihydro-2,6-dimethyl-4-(3-nitrophenyl)pyridine-3,5-dicarboxylic acid propyl methyl ester;
1,4-dihydro-2,6-dimethyl-4-(3-nitrophenyl)pyridine-3,5-dicarboxylic acid isopropyl methyl ester;
1,4-dihydro-2,6-dimethyl-4-(4-nitrophenyl)pyridine-3,5-dicarboxylic acid ethyl methyl ester;
1,4-dihydro-2,6-dimethyl-4-(4-nitrophenyl)pyridine-3,5-dicarboxylic acid propyl methyl ester;
1,4-dihydro-2,6-dimethyl-4-(4-nitrophenyl)pyridine-3,5-dicarboxylic acid isopropyl methyl ester;
1,4-dihydro-2,6-dimethyl-4-(2-trifluorophenyl)pyridine-3,5-dicarboxylic acid ethyl methyl ester;
1,4-dihydro-2,6-dimethyl-4-(2-trifluorophenyl)pyridine-3,5-dicarboxylic acid propyl methyl ester;
1,4-dihydro-2,6-dimethyl-4-(2-trifluorophenyl)pyridine-3,5-dicarboxylic acid isopropyl methyl ester;
1,4-dihydro-2,6-dimethyl-4-(3-trifluorophenyl)pyridine-3,5-dicarboxylic acid ethyl methyl ester;
1,4-dihydro-2,6-dimethyl-4-(3-trifluorophenyl)pyridine-3,5-dicarboxylic acid propyl methyl ester;
1,4-dihydro-2,6-dimethyl-4-(3-trifluorophenyl)pyridine-3,5-dicarboxylic acid isopropyl methyl ester;
1,4-dihydro-2,6-dimethyl-4-(4-trifluorophenyl)pyridine-3,5-dicarboxylic acid ethyl methyl ester;
1,4-dihydro-2,6-dimethyl-4-(4-trifluorophenyl)pyridine-3,5-dicarboxylic acid propyl methyl ester;
1,4-dihydro-2,6-dimethyl-4-(4-trifluorophenyl)pyridine-3,5-dicarboxylic acid isopropyl methyl ester;
1,4-dihydro-2,6-dimethyl-4-(2-cyanophenyl)pyridine-3,5-dicarboxylic acid ethyl methyl ester;
1,4-dihydro-2,6-dimethyl-4-(2-cyanophenyl)pyridine-3,5-dicarboxylic acid propyl methyl ester;
1,4-dihydro-2,6-dimethyl-4-(2-cyanophenyl)pyridine-3,5-dicarboxylic acid isopropyl methyl ester;
1,4-dihydro-2,6-dimethyl-4-(3-cyanophenyl)pyridine-3,5-dicarboxylic acid ethyl methyl ester;
1,4-dihydro-2,6-dimethyl-4-(3-cyanophenyl)pyridine-3,5-dicarboxylic acid propyl methyl ester;
1,4-dihydro-2,6-dimethyl-4-(3-cyanophenyl)pyridine-3,5-dicarboxylic acid isopropyl methyl ester;
1,4-dihydro-2,6-dimethyl-4-(4-cyanophenyl)pyridine-3,5-dicarboxylic acid ethyl methyl ester;
1,4-dihydro-2,6-dimethyl-4-(4-cyanophenyl)pyridine-3,5-dicarboxylic acid propyl methyl ester;
1,4-dihydro-2,6-dimethyl-4-(4-cyanophenyl)pyridine-3,5-dicarboxylic acid isopropyl methyl ester;
1,4-dihydro-2,6-dimethyl-4-(2-pyridyl)pyridine-3,5-dicarboxylic acid ethyl methyl ester;
1,4-dihydro-2,6-dimethyl-4-(2-pyridyl)pyridine-3,5-dicarboxylic acid propyl methyl ester;
1,4-dihydro-2,6-dimethyl-4-(2-pyridyl)pyridine-3,5-dicarboxylic acid isopropyl methyl ester;
1,4-dihydro-2,6-dimethyl-4-(3-pyridyl)pyridine-3,5-dicarboxylic acid ethyl methyl ester;
1,4-dihydro-2,6-dimethyl-4-(3-pyridyl)pyridine-3,5-dicarboxylic acid propyl methyl ester;
1,4-dihydro-2,6-dimethyl-4-(3-pyridyl)pyridine-3,5-dicarboxylic acid isopropyl methyl ester;
1,4-dihydro-2,6-dimethyl-4-(4-pyridyl)pyridine-3,5-dicarboxylic acid ethyl methyl ester;
1,4-dihydro-2,6-dimethyl-4-(4-pyridyl)pyridine-3,5-dicarboxylic acid propyl methyl ester; and
1,4-dihydro-2,6-dimethyl-4-(4-pyridyl)pyridine-3,5-dicarboxylic acid isopropyl methyl ester.

6. The method of claim 5, said method comprising administering to said living body an effective amount of 1,4-dihydro-2,6-dimethyl-4-(3-nitrophenyl)pyridine-3,5-dicarboxylic acid ethyl methyl ester (Nitrendipine).

* * * * *